United States Patent [19]

Levy

[11] Patent Number: 5,306,143
[45] Date of Patent: Apr. 26, 1994

[54] DENTAL HYGIENE APPLIANCE

[75] Inventor: Philippe Levy, San Clemente, Calif.

[73] Assignee: Laser Medical Technology, Inc., San Clemente, Calif.

[21] Appl. No.: 961,341

[22] Filed: Oct. 15, 1992

[51] Int. Cl.⁵ ............................ A61C 1/00; A61C 3/00; A46B 9/04

[52] U.S. Cl. ........................................ 433/29; 15/167.1

[58] Field of Search ................ 433/29, 215, 216, 229; 15/167.1, 167.2; 362/109, 804

[56] References Cited

U.S. PATENT DOCUMENTS

| | | | |
|---|---|---|---|
| 2,397,757 | 4/1946 | Schwedersky | 15/160 |
| 3,261,978 | 7/1966 | Brenman | 15/167.1 X |
| 4,273,535 | 6/1981 | Yamamoto et al. | 433/216 |
| 4,779,173 | 10/1988 | Carr et al. | 362/109 |
| 5,030,090 | 7/1991 | Maeda et al. | 433/29 |
| 5,160,194 | 11/1992 | Feldman | 15/167.1 X |

FOREIGN PATENT DOCUMENTS 9011728 10/1990 World Int. Prop. O. .......... 433/216

*Primary Examiner*—Gene Mancene
*Assistant Examiner*—Nicholas D. Lucchesi
*Attorney, Agent, or Firm*—Spensley Horn Jubas & Lubitz

[57] ABSTRACT

A dental hygiene appliance for brushing teeth composed of a handle; a brushing head connected to the handle and a set of tooth brushing bristles projecting in a given direction from the head; a source of monochromatic radiation having a given wavelength; and elements for directing the radiation from the head in a direction having at least a component in the given direction; wherein the elements for directing radiation are structurally separate from the bristles.

15 Claims, 1 Drawing Sheet

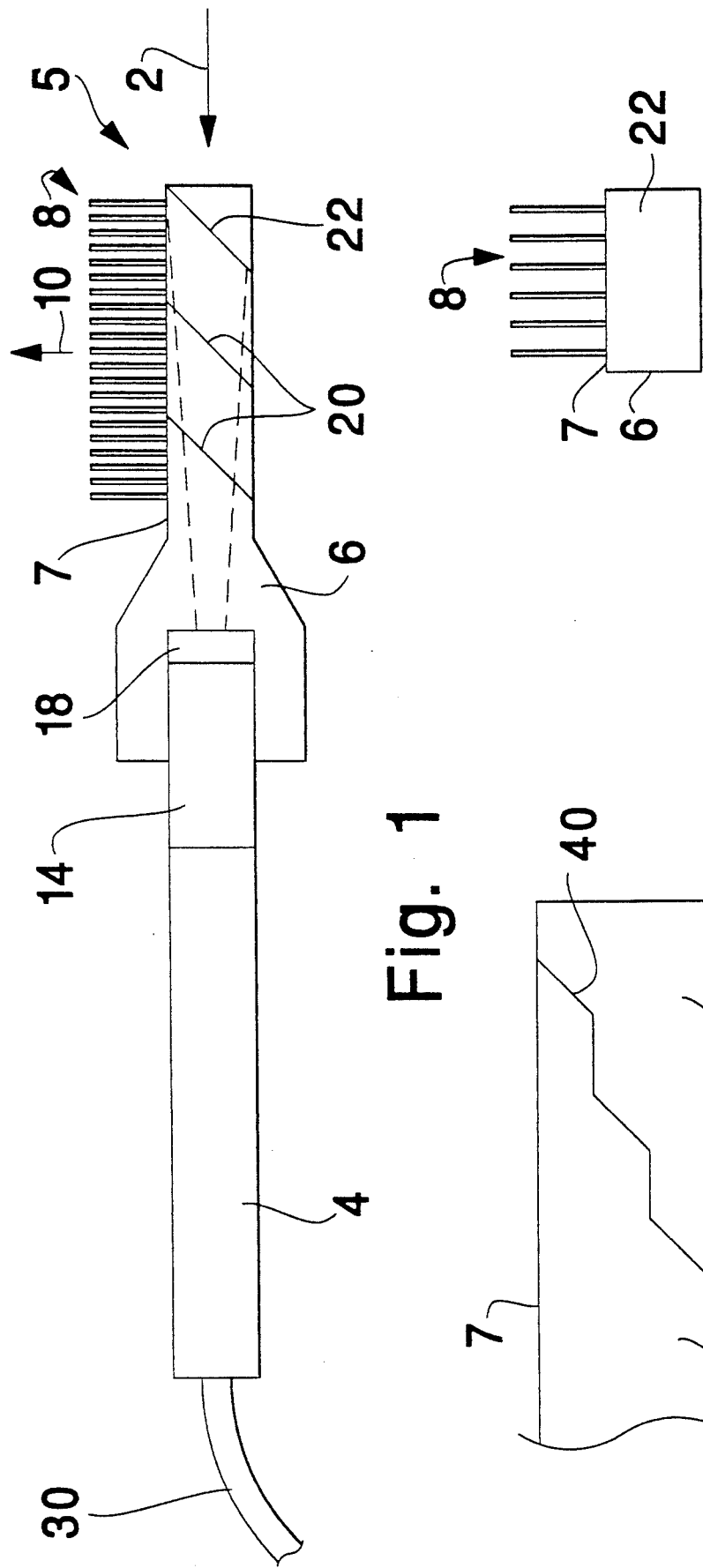

DENTAL HYGIENE APPLIANCE

BACKGROUND OF THE INVENTION

The present invention relates to dental hygiene appliances, and particularly toothbrushes equipped to apply radiation to tooth surfaces.

It has been proposed in the art to equip a toothbrush with a light source which can illuminate the region being brushed. The purpose of such devices is to aid the brushing operation by better illuminating the portion of the teeth being brushed. A device of this type is disclosed in U.S. Pat. No. 4,779,173, where the toothbrush bristles are plastic filaments which conduct radiation from a light source in the handle of the brush. This patent also discloses earlier prior art including a dental cleaning apparatus in which the head portion or bristle holding portion is eliminated.

It is also known in the art that laser radiation can have a variety of beneficial effects on teeth.

U.S. Pat. No. 5,030,090 discloses a tooth brush having a bundle of bristles constituted by optical fibers which are coupled to a semiconductor laser. The fibers constitute the bristles of the toothbrush. This patent discloses that the radiation produced by a semiconductor laser can be used for treating or preventing gingivitis and other oral diseases, and specifically can serve to reduce pain and inflammation and to improve blood circulation.

One of the characteristics of the device as disclosed in the above-cited patents is that they employ filaments which are capable of functioning as both optical fibers and brushing bristles. One problem with devices of this type is that filaments which are capable of functioning as optical fibers can not be given the mechanical characteristics required to permit them to function in an optimum manner as brushing bristles. In particular, if the filaments must be fabricated to function as optical fibers, it will prove difficult to give them the durability desired for brushing bristles.

SUMMARY OF THE INVENTION

It is an object of the present invention to provide a novel dental hygiene appliance which applies radiation having a selected wavelength to tooth surfaces while those surfaces are being brushed.

Another object of the invention is to provide an appliance of this type in which the toothbrush bristles are employed only for brushing, and may therefore be selected solely on the basis of the characteristics required for performing that function.

Another object of the invention is to employ such an appliance in a manner to enhance the effectiveness of the brushing action, possibly with the aid of a chemical product which facilitates observation and/or removal of one or more substances of the type which form deposits on teeth.

The above and other objects are achieved, according to the present invention, by a dental hygiene appliance for brushing teeth comprising: a handle; a brushing head connected to the handle and a set of tooth brushing bristles projecting in a given direction from the head; a source of monochromatic radiation having a given wavelength; and means for directing the radiation from the head in a direction having at least a component in the direction; given wherein the means for directing radiation are structurally separate from the bristles.

Objects according to the invention are further achieved by supplying with the appliance a chemical product which is capable and/or facilitating removal, of a substance which forms deposits on teeth and when that substance is irradiated by the radiation having a given wavelength. Then, since the brushing action is performed on, and the radiation is being applied to, substantially the same tooth areas, the brushing action in the presence of that chemical product will facilitate thorough cleaning of the teeth.

BRIEF DESCRIPTION OF THE DRAWING

FIG. 1 is a simplified side elevational view, partly in cross section, illustrating the basic components of an embodiment according to the present invention.

FIG. 2 is an end elevational view in the direction of the arrow 2 of FIG. 1.

FIG. 3 is a detail view illustrating a modified version of a portion of the appliance of FIG. 1.

DESCRIPTION OF THE PREFERRED EMBODIMENTS

The basic components of an appliance according to the present invention include, as shown in FIGS. 1 and 2, a handle 4 and a brushing head 5. Brushing head 5 is constituted by a body 6 having a base surface 7 from which a set of tooth brushing bristles 8 project. The composition and form of bristles 8, and the manner in which bristles 8 are secured to body 6, conform to conventional practice in the toothbrush art.

Appliances according to the present invention are further provided with means for directing monochromatic radiation of a selected type from body 6 in the direction of arrow 10, which is generally parallel to the direction in which bristles 8 project from body 6. However, in appliances according to the invention, the radiation is not guided by the bristles themselves, but is emitted generally via base surface 7 of body 6.

In the embodiment illustrated in FIGS. 1 and 2, handle 4 is provided with a laser device 14, for example a semiconductor laser, and brushing head 5 is provided with a lens 18, one or more semitransparent mirrors 20 and a fully reflecting mirror 22. Radiation produced by laser 14 may be in the form of a small diameter collimated beam extended along an axis corresponding to the longitudinal axis of handle 4 and head 5. Mirrors 20 and 22 may be oriented at an angle of 45° to the beam axis and lens 18 is constructed and arranged to give the laser radiation beam a slightly diverging form such that the beam will diverge to an area essentially coextensive with the area occupied by mirror 22.

Body 6 may itself be made of a plastic which is transparent to the laser radiation so that portions of the radiation will be reflected in the direction 10 by mirrors 20, and the remaining radiation will be reflected by mirror 22. The optical system constituted by lens 18 and mirrors 20, 22 is arranged to cause radiation to traverse an area at least approximately coextensive with the area covered by the tips of bristles 8. However, the radiation area may, depending on the particular operations to be performed, extend over a smaller or larger area.

In the embodiment illustrated in FIGS. 1 and 2, handle 4 includes a power cord 30 which may be plugged into a wall outlet in order to supply operating power to laser 14. Alternatively, handle 4 could be constructed as a holder for a replaceable or rechargeable battery which supplies the necessary operating power. In addition, in the embodiment illustrated in FIGS. 1 and 2, brushing head 5 is readily detachable from handle 4. This allows a plurality of brushing heads 5, each used by a different individual, to be mounted on head 4 for use. In addition, as shown in FIGS. 1 and 2, lens 18 may form a unit with head 2, so that each of the brushing heads 5 need not be provided with its own lens. This would reduce the cost of manufacturing each head 5.

FIG. 3 shows an alternative embodiment of the brushing head, which can be constituted by two plastic pieces 34 and 36 joined together along a plane 40 having a series of surfaces which are inclined at an angle of 45° to the axis of the radiation emitted by laser 14. Plane 40 is made to be a reflecting surface by an appropriate coating or finishing process. In FIG. 3, the bristles 8 are not shown, for the sake of simplicity.

The radiation provided in an appliance according to the present invention has a wavelength as well as an intensity, selected to have a desired effect on one or more substance which may become deposited on tooth surfaces and which it is desired to remove. Typical substances of this type include bacteria, tartar and calculus, all of which contribute or are precursors, to tooth decay. In addition, when certain chemical products are brought into contact with one or another of these substances, the application of radiation having an appropriate wavelength and energy content can render the substance or substances visible and/or can help to remove those substances from tooth surfaces.

Thus, in accordance with the invention, an appliance of the type described above is used in cooperation with such a chemical product, which may be incorporated into a toothpaste, tooth gel or tooth powder, formulated and marketed for use specifically with the appliance.

By way of example, one of the purposes of tooth brushing is to remove bacteria which have collected on tooth surfaces, frequently in pits and fissures in the tooth enamel. It is known that regardless of the care exercised and time spent in a brushing session, some of the bacteria deposits may not be dislodged and removed from the tooth surfaces. It is also known that there are chemical products, known as disclosing solutions, which can make any deposited bacteria visible. There are other chemical products, which may be preferable to the conventional disclosing solutions, which will react with bacteria in such a manner as to render the bacteria visible in the presence of radiation having a certain wavelength. Such product can be provided as an ingredient of a special toothpaste, tooth gel or tooth powder supplied with the appliance according to the invention.

When such a tooth cleaning preparation is employed, the chemical product will render any existing bacteria visible under the radiation produced by source 14, so that brushing can be continued until the user can observe that all bacteria have been removed from all visible tooth surfaces. While it would be more difficult to carry out this procedure on lingual tooth surfaces, this would be possible, if brushing were carried out while viewing those surfaces with a mirror.

In further accordance with the invention, the chemical product may be selected to render tartar or calculus visible, while the appliance is then utilized to remove those materials. Possibly, special brush heads with appropriate bristles could be provided for this purpose.

In further accordance with the invention, use may be made of a product which reacts with bacteria, tartar or calculus in such a manner that radiation of an appropriate wavelength will have the effect of removing the bacteria, tartar or calculus, or of altering the nature of the bacteria, tartar, or calculus, as by softening it, in a manner to facilitate complete removal by the brushing action.

According to one exemplary embodiment of the invention, the chemical product consists of or contains nigrosin and the radiation source produces radiation at a wavelength of between $1\mu$ and $6\mu$. The radiation source may be, for example, an Nd:YAG laser. The source will be adjusted to emit radiation at an energy level selected on the basis of the expected concentration of nigrosin in the material to be treated.

Nigrosin will stain, for example, cariogenic bacteria or streptococcus faecalis black so that this bacteria, or any other substance absorbing nigrosin, will readily absorb the laser radiation.

According to another possibility, the chemical product can be sudan red as a vital stain when the radiation source is an argon laser.

In both cases, the radiation energy density could be made sufficiently high to directly vaporize the stained substance. For example, in the case where streptococcus faecalis is stained with nigrosin and irradiated by an Nd:YAG laser, this effect can be achieved with an energy density of the order of 10 $J/cm^2$.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A dental hygiene appliance for brushing teeth comprising:
    a handle;
    a brushing head connected to said handle and a set of tooth brushing bristles projecting in a given direction from said head;
    a laser contained in said handle and constituting a source of monochromatic radiation having a given wavelength;
    means for directing the radiation from said head in a direction having at least a component in the given direction; and
    means for delivering the radiation to said means for direction radiation;
    wherein said means for directing radiation are structurally separate from said bristles.

2. An appliance as defined in claim 1 wherein said bristles are made of a material selected to perform an effective brushing action on teeth.

3. An appliance as defined in claim 2 wherein said bristles are made of a natural material.

4. An appliance as defined in claim 2 wherein said bristles are made of nylon.

5. An appliance as defined in claim 1 wherein said means for directing radiation comprise optical components in said head for directing the radiation at least partly around said bristles.

6. An appliance as defined in claim 1 wherein said means for delivering the radiation are in said handle.

7. An appliance as defined in claim 5 further comprising a battery disposed in said handle and constituting a power source for said radiation source.

8. An appliance as defined in claim 6 wherein said brushing head is readily detachable from said handle.

9. An appliance as defined in claim 8 further comprising a battery disposed in said handle and constituting a power source for said radiation source.

10. An appliance as defined in claim 1 wherein radiation having said given wavelength is capable of rendering visible a substance present on a tooth.

11. An appliance as defined in claim 1 in combination with a supply of a given chemical product, wherein radiation having the given wavelength is capable of rendering visible a substance present on a tooth when the substance has been contacted by the given chemical product.

12. The combination as defined in claim 11 wherein said supply of the given chemical product comprises a mass of toothpaste containing the given product.

13. An appliance as defined in claim 1 wherein said radiation having a given wavelength is capable of removing a substance present on a tooth.

14. An appliance as defined in claim 1 in combination with a supply of a given chemical product, wherein radiation having the given wavelength is capable of removing a substance present on a tooth when the substance has been contacted by the given chemical product.

15. The combination as defined in claim 14 wherein said supply of the given chemical product comprises a toothpaste containing the given product.

* * * * *